United States Patent [19]

Diana

[11] Patent Number: 5,364,865
[45] Date of Patent: Nov. 15, 1994

[54] PHENOXY- AND PHENOXYALKYL-PIPERIDINES AS ANTIVIRAL AGENTS

[75] Inventor: Guy D. Diana, Stephentown, N.Y.

[73] Assignee: Sterling Winthrop Inc., New York, N.Y.

[21] Appl. No.: 998,498

[22] Filed: Dec. 30, 1992

[51] Int. Cl.$^5$ ............... A61K 31/445; C07D 401/04; C07D 401/14; C07D 241/10
[52] U.S. Cl. ................... 514/318; 514/252; 514/256; 514/326; 544/334; 544/335; 544/336; 544/409; 546/194; 546/209; 546/210
[58] Field of Search ............ 544/242, 334, 335, 336, 544/409; 546/193, 194, 209, 210; 514/318, 252, 273, 256, 326

[56] References Cited

U.S. PATENT DOCUMENTS

| | | | |
|---|---|---|---|
| 4,939,267 | 7/1990 | Diana | 548/237 |
| 4,992,433 | 2/1991 | Stokbroekx | 544/238 |
| 5,100,893 | 3/1992 | Stokbroekx | 544/237 |

FOREIGN PATENT DOCUMENTS 0320032 11/1988 European Pat. Off. .
0435381 12/1990 European Pat. Off. .

OTHER PUBLICATIONS

Stuart-Harris et al., "The Background to Chemotherapy of Virus Diseases", C. C. Thomas, pp. 76–77 (1965).

*Primary Examiner*—Celia Chang
*Attorney, Agent, or Firm*—Richard A. Hake; Paul E. Dupont

[57] ABSTRACT

Compounds of the formula

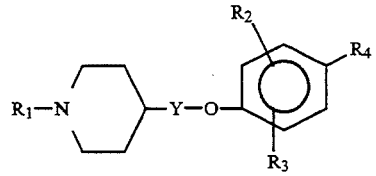

wherein
$R_1$ is selected from

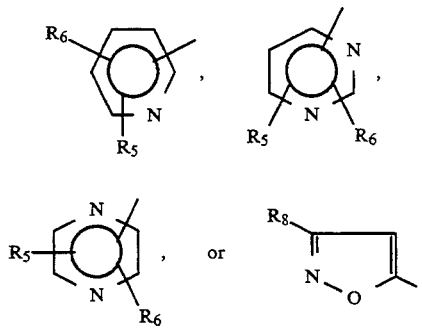

Y is a bond or lower alkylene;
$R_2$ and $R_3$ are independently hydrogen, lower-alkyl or halogen;
$R_4$ is

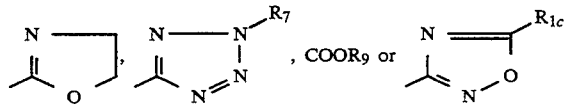

$R_5$ is hydrogen, lower-alkyl or halogen;
$R_6$ is hydrogen, lower-alkyl or halogen;
$R_7$ is hydrogen or lower-alkyl;
$R_8$ is hydrogen, lower-alkyl, or trifluoromethyl;
$R_9$ is lower-alkyl;
$R_{10}$ is lower-alkyl, trifluoromethyl or difluoromethyl;
or pharmaceutically acceptable acid addition salts thereof are useful as antiviral agents.

24 Claims, No Drawings

PHENOXY- AND PHENOXYALKYL-PIPERIDINES AS ANTIVIRAL AGENTS

BACKGROUND OF THE INVENTION a) Field Of the Invention

This invention relates to novel substituted phenoxy-piperidinyl and phenoxyalkylpiperidinyl compounds, their pharmaceutical compositions and a method for the treatment or prevention of viral infection.

b) Information Disclosure Statement

European Patent Application No. 320032, published Nov. 17, 1986, discloses compounds having the formula

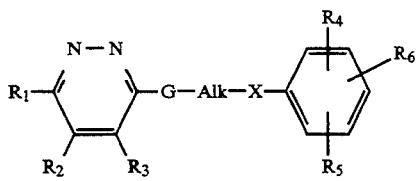

wherein:

$R_1$ is hydrogen, $C_{1-6}$alkyl, halo, hydroxy, mercapto, trifluoromethyl, amino, mono or di($C_{1-6}$alkyl) amino, cyano, $C_{1-6}$alkyloxy, aryloxy, aryl$C_{1-6}$alkyloxy, $C_{1-6}$alkylthio, arylthio, $C_{1-6}$alkylsulfinyl, $C_{1-6}$alkylsulfonyl, arylsulfinyl, arylsulfonyl, $C_{1-6}$alkoxycarbonyl, $C_{1-6}$alkylcarbonyl, or aryl;

$R_2$ and $R_3$ each independently are hydrogen or $C_{1-6}$alkyl, or $R_2$ and $R_3$ combined may form a bivalent radical of formula —CH=CH—CH=CH—

Alk is an alkane chain 0–6 carbons long

G is a bivalent radical of formula

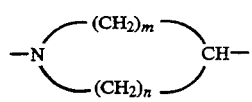

n is 2–3 carbons
m is 2–3 carbons
X is O, S, $NR_8$ or a direct bond; said $R_8$ being hydrogen or $C_{1-6}$alkyl.
$R_4$, $R_5$ and $R_6$ are independently H, halo, $C_1$-$C_6$ alkyl, amino, cyano or nitro. The compounds are stated to have antiviral activity.

European Patent Application 435381, published Jul. 3, 1991, discloses pyridazinamines of formula

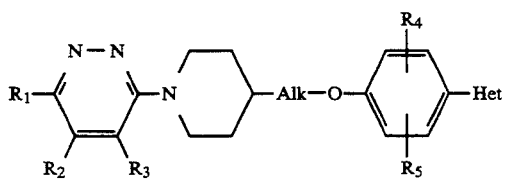

wherein
$R_1$ is hydrogen, $C_{1-4}$alkyl, halo, hydroxy, trifluoromethyl, cyano, $C_{1-4}$alkoxy, $C_{1-4}$alkylthio, $C_{1-4}$alkylsulfinyl, $C_{1-4}$alkylsulfonyl, $C_{1-4}$alkyloxycarbonyl, $C_{1-4}$alkylcarbonyl or aryl;
$R_2$ and $R_3$ are hydrogen or $C_{1-4}$alkyl;
Alk is $C_{1-4}$alkanediyl;
$R_4$ and $R_5$ are hydrogen, $C_{1-4}$alkyl or halo; and
Het is

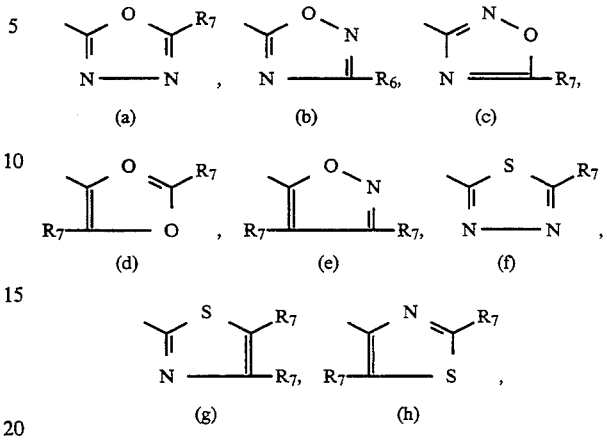

wherein
$R_6$ is hydrogen, $C_{1-6}$alkyl; hydroxy$C_{1-6}$alkyl; $C_{3-6}$cycloalkyl; aryl; aryl$C_{1-4}$alkyl; $C_{1-4}$alkyloxy$C_{1-4}$alkyl; $C_{3-6}$cyclo-alkyl$C_{1-4}$alkyl; trifluoromethyl or amino;
each $R_7$ independently is hydrogen; $C_{1-6}$alkyl; $C_{3-6}$cyclo-alkyl; aryl; aryl-$C_{1-4}$alkyl; $C_{1-4}$alkyloxy$C_{1-4}$alkyl; $C_{3-6}$cyclo-alkyl-$C_{1-4}$alkyl or trifluoromethyl; and
each aryl independently is phenyl or phenyl substituted with 1 or 2 substituents each independently selected from halo, $C_{1-4}$alkyl, trifluoromethyl, $C_{1-4}$alkyloxy or hydroxy. The compounds are stated to have antiviral activity.

SUMMARY OF THE INVENTION

It has now been found that substituted phenoxy- and phenoxyalkylpiperidinyl derivatives are effective as antiviral agents.

Accordingly the present invention relates to compounds of the formula

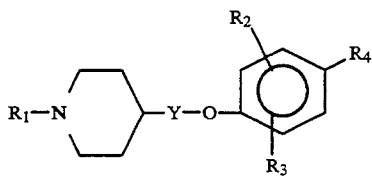

wherein
$R_1$ is

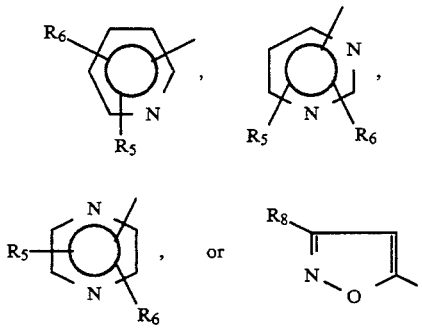

$R_2$ and $R_3$ are independently hydrogen, lower-alkyl or halogen;

$R_4$ is

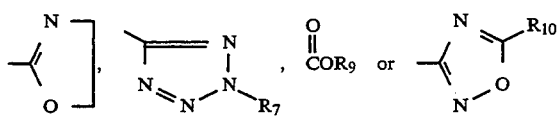

$R_5$ is hydrogen, halogen, or lower-alkyl;
$R_6$ is hydrogen, halogen, or lower-alkyl;
$R_7$ is hydrogen or lower-alkyl;
$R_8$ is hydrogen, lower-alkyl or trifluoromethyl;
$R_9$ is lower-alkyl
$R_{10}$ is lower-alkyl, difluoromethyl or trifluoromethyl; and
Y is a bond or lower-alkylene;
or pharmaceutically acceptable acid addition salts thereof.

Falling within the ambit of the invention are pharmaceutical compositions of compounds of formula I.

In a method of use aspect, the invention relates to a method for combating or preventing viral infection in mammalian hosts comprising administering an effective amount of a compound of formula I to a patient in need of such treatment.

DETAILED DESCRIPTION INCLUSIVE OF PREFERRED EMBODIMENTS

Lower-alkyl refers to a straight or branched hydrocarbon radical of from 1 to about 4 carbon atoms such as methyl, ethyl, isopropyl, butyl, sec-butyl, and the like. Lower alkylene refers to a linear or branched divalent hydrocarbon radical of from 1 to about 4 carbon atoms such as methylene, ethylene, 1,3-propylene, 1,3-butylene, and the like. Halogen refers to the common halogens fluorine, chlorine, bromine and iodine.

The term inert or noninteracting solvent refers to a solvent that does not take part in the reaction.

Certain abbreviations used hereinbelow are defined as follows:
triphenyl phosphine (TPP);
diethyl azidodicarboxylate (DEAD);
disopropylethylamine (DIPEA); and
ether refers to diethylether.

Preferred compounds of Formula I are compounds wherein Y is a bond, methylene or ethylene and $R_7$, $R_8$ and $R_9$ are lower-alkyl.

Compounds of Formula I are prepared by reacting a 1-$R_1$-4-hydroxy or 1-$R_1$-4-hydroxyalkyl piperidine (II), where Y is a bond or lower-alkylene, respectively

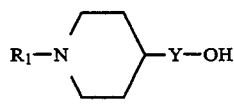

with a phenol III

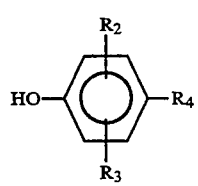

in the presence of triphenylphosphine and diethyl azodicarboxylate in an inert solvent such as methylene chloride, at a temperature of about 0° C. to the reflux temperature of the reaction mixture.

In a preferred method the compounds of Formula I where $R_1$ is substituted or unsubstituted pyridinyl, pyrimidinyl or pyrazinyl are prepared by reacting a phenoxy or phenoxyalkyl piperidine IV

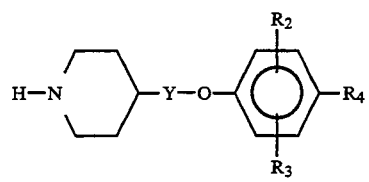

with an appropriate halopyridine, halopyrimidine, or halopyrazine ($R_1$—X, X=halogen) optionally in the presence of a base, preferably an organic base, e.g. DIPEA. The reaction is carried out in an inert solvent such as NMP at a temperature from about 25° C. to the boiling point of solvent. If desired, the reaction may be carried out in a medium that functions as both base and solvent, e.g. DIPEA.

The intermediates of Formula IV are prepared by reacting phenol III with a 1-benzyl-4-hydroxy or 1-benzyl-4-hydroxyalkyl piperidine V.

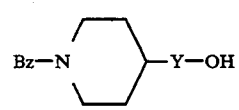

in the presence of triphenyl phosphine and diethyl azodicarboxylate as described above. The benzyl group is then removed by conventional means such as reaction with hydrogen using a catalytic amount of palladium on carbon.

Intermediates of Formula II where $R_1$ is substituted or unsubstituted pyridinyl, pyrimidinyl or pyrazinyl are prepared by reacting the appropriate 4-hydroxy or 4-hydroxyalkyl piperidine with an appropriate halopyridine, halopyrimidine, or halopyrazine ($R_1$—X, X=halogen) as described above for preparation of the compounds of formula I from intermediate IV. The halopyridines, halopyrimidines and halopyrazines ($R_1$—X) are known in the art and are generally commercially available.

Intermediates of Formula II where $R_1$ is isoxazole or substituted isoxazole are prepared by reacting 5-amino-3-$R_7$ isoxazole VI

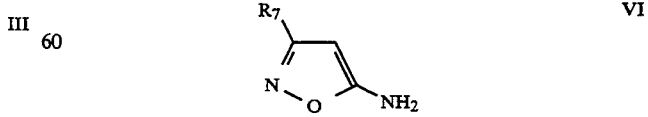

and allyl acrylate in a noninteracting solvent, for example NMP, and base, for example $K_2CO_3$, between ambient temperature and the boiling temperature of the solvent yielding a compound of formula VII

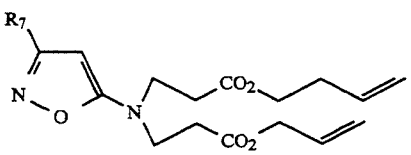

VII

Reduction of VII, for example with a metal hydride such as lithium aluminum hydride, in an inert solvent such as benzene at a temperature from −50° C. to the boiling point of the solvent affords VIII

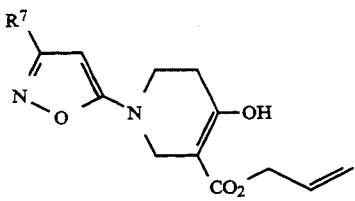

VIII which is reacted with tetrakis-triphenylphosphine palladium yielding IX

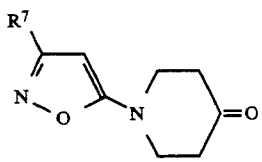

IX

Ketone IX is reduced using conventional methods, e.g. a complex metal hydride, to give a compound of formula II wherein $R_1$ is 3-$R_7$-isoxazol-5-yl and Y is a bond, or ketone IX is treated with an appropriate Wittig reagent, e.g. a lower-alkylidene phosphorane or phosphoric-lower alkanoate and the resulting product reduced catalytically and/or with a metal hydride, for example $NaAlH_2$ $(OCH_2CH_2OCH_3)_2$, commercially available as Vitride ™ and the like, to give a compound of formula II ($R_1$=3-$R_7$-isoxazol-5-yl, Y=lower-alkylene).

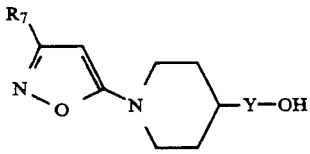

5-Amino-3-$R_7$-isoxazoles wherein $R_7$ is hydrogen or lower-alkyl are known or may be prepared by known methods. [Stevens et al., Tet. Let. 25(41) p. 4587-90 (1984); Himbert et al., Liebigs Ann. Chem. 403 (1990)]. Intermediate phenols of Formula III wherein $R_4$ is $COOR_9$ are generally known compounds. Intermediate phenols of Formula III wherein $R_4$ is oxazolin-2-yl

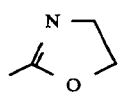

are disclosed in detail in Diana U.S. Pat. No. 4,939,267, incorporated herein by reference.

Intermediate phenols of Formula III wherein $R_4$ is tetrazolyl are prepared by reaction of 4-Z-O-$R_2$-$R_3$-benzonitrile, in which Z is a protecting group easily cleaved from an aromatic ether such as methyl, benzyl and the like, with sodium azide or the like in a non-interacting solvent between ambient temperature and the boiling point of the solvent yielding X, where $R_7$ is hydrogen.

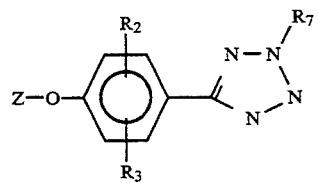

X

If desired the 5- (4-Z-O-$R_2$-$R_3$-phenyl)tetrazole X is alkylated by reaction with a base and a lower-alkyl halide $R_7$-X in a non-interacting solvent between 0° C. and the boiling point of the solvent to give compounds of formula X, $R_7$=lower-alkyl.

The protective group Z is removed by acid cleavage, for example by reaction with HBr or $BBr_3$ to give the 2-$R_7$-5-(4-hydroxy-$R_2$-$R_3$-phenyl)-2H-tetrazole (X, Z=H, $R_7$=lower-alkyl).

Intermediate phenols of formula III where $R_4$ is oxadiazolyl

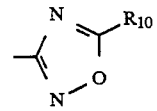

are prepared from the appropriate 4-Z-O-$R_3$-$R_4$-benzonitrile by reaction with hydroxylamine hydrochloride in a noninteracting solvent, preferably an alkanol, for example methanol, ethanol, n-butanol and the like, in the presence of a base, such as potassium carbonate, or in a preferred method an alkali metal salt of a carboxylic acid such as sodium trifluoroacetate or sodium acetate, at a temperature between ambient and the boiling point of the solvent. The product thus obtained is then reacted with an acid anhydride of formula $(R_{10}CO)_2O$, for example trifluoroacetic anhydride, or acetic anhydride, at a temperature between ambient and the boiling point of the reaction mixture in a basic solvent such as pyridine.

The protective group Z is then removed by acid cleavage as described above.

The intermediates of Formula V where Y is a bond is commercially available and can be benzylated by conventional means well known in the art.

Intermediates of Formula V where Y is alkylene are known or may be prepared by reducing the appropriate esters of formula XI where Y' is lower-alkylene having one less carbon atom than Y.

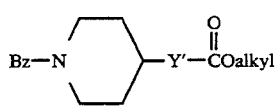

XI

The reduction of the ester by methods well known in the art, such as complex metal hydride, affords primary alcohols as products. An alkylating agent such as alkyl lithium or a grignard reagent may be reacted with the ester to afford branched hydroxyalkylene, if desired.

It will, of course, be appreciated that the sequence in which the above-described reactions are carried out can be varied. For example, nitrile XII is obtained by reacting a piperidine of formula II with 4-hydroxy-$R_2$-$R_3$-benzonitrile (III, $R_4$=CN) under the conditions described above for preparing the compounds of formula I by reacting piperidine II with phenol III

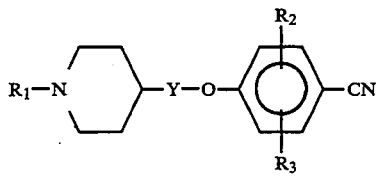

XII

Nitrile XII in turn is converted to compounds of formula I where $R_4$ is tetrazolyl or oxadiazolyl by reaction with sodium azide or hydroxylamine as described above in preparation of phenols III where $R_4$ is tetrazolyl or oxadiazolyl, respectively.

Alternatively, intermediate XII can be prepared by the coupling of 4-hydroxy-$R_2$-$R_3$-benzonitrile and a piperidine of formula V as described above for the preparation of intermediates IV to give XIII

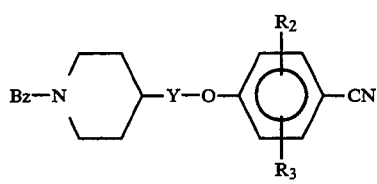

XIII which, after removal of the benzyl group, is reacted with an appropriate halopyridine, halopyrimidine or halopyrazine ($R_1$=X), as described above for the preparation of compounds of formula I, to give a compound of formula XII.

Thus it will be appreciated that neither the timing of the elaboration of the heterocyclic substituent $R_4$ nor the order of assembly of the intermediates, is crucial to the successful synthesis of compounds of formula I.

The compounds of the invention are sufficiently basic to form acid-addition salts, and are useful both in the free base form and the form of acid-addition salts, and both forms are within the purview of the invent ion. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions.

Examples of appropriate acid-addition salts include but at not limited to the hydrochloride, hydrobromide, sulfate, acid sulfate, maleate, citrate, tartrate, methanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate products, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared spectroscopy and in certain cases by, ultraviolet, nuclear magnetic resonance or mass spectroscopy. The course of the reactions was monitored by thin layer chromatography (TLC) or gas-liquid chromatography (GLC).

The following examples will further illustrate the invention without, however, limiting it thereto.

PREPARATION OF INTERMEDIATES

Preparation 1

Preparation of 2-methyl-5-(4-hydroxyphenyl)-2H-tetrazole (Formula III: $R_2$=$R_3$=H, $R_4$=2-methyl-2H-tetrazol-5-yl)

a) A mixture containing 325 g of 4-cyanophenol, 346 mL of benzyl chloride and 758 g of potassium carbonate in 1.2 L of NMP was heated at 95° C. with stirring for 1.5 hrs. The reaction mixture was cooled to room temperature and poured into 5 L of cold water. The resulting white solid was collected, washed with water and hexanes and dried at 70° C. in vacuo giving 570.0 g of 4-benzyloxybenzonitrile.

b) A mixture of 285 g of the nitrile, 262.5 g triethylamine hydrochloride and 124 g of sodium azide in 1.5 L of DMF under nitrogen was stirred under reflux for 18 hrs. The reaction mixture was cooled to room temperature, poured into 4 L of cold water and acidified with 3N HCl. The resulting white solid was collected, washed with water and dried at 60° C. in vacuo for 48 hrs to give 337 g of 5-(4 -benzyloxyphenyl)-tetrazole.

c) To a stirred solution containing 337 g of the tetrazole and 362 mL of DIPEA in 1 L of NMP cooled to 18° C. under $N_2$ was added dropwise over 1.5 hrs 200 g of methyl iodide in 170 mL NMP. After stirring an additional hour at room temperature, the reaction mixture was diluted with 340 mL of water and cooled to 18° C. The resulting solid was collected, washed with water, recrystallized from ethanol and dried in vacuo at 50° C. to give 232.3 g of 2-methyl-5-(4-benzyloxyphenyl)-2H-tetrazole. (Formula X: $R_2$=$R_3$=hydrogen, $R_7$=methyl, Z=benzyl).

d) A mixture containing 214.2 g of the methyl tetrazole, 140 mL of concentrated hydrochloric acid and 1.08 L of glacial acetic acid was heated under reflux for 19 hrs. Most of the acetic acid was removed by evaporation under reduced pressure at 60° C. and the resulting slurry was diluted with 1.5 L of cold water. The resulting solid was collected, washed with water and dried. Recrystallization from ethanol afforded, after drying at 60° C. for 20 hrs, 104.3 g of 2-methyl-5-(4-hydroxyphenyl)-2H-tetrazole (Formula III: $R_2$=$R_3$=H, $R_4$=2-methyl-2H-tetrazol-5-yl).

Preparation 2

Preparation of 2-methyl-5-(4-hydroxy-3,5-dimethylphenyl)-2H-tetrazole (Formula III: $R_2=3\text{-}CH_3$, $R_3=5\text{-}CH_3$, $R_4=2\text{-methyl-2H-tetrazol-5-yl}$)

2-Methyl-5-(3,5-dimethyl-4-hydroxyphenyl)-2H-tetrazole was prepared by the procedure described above in Preparation 1 starting with 2,6-dimethyl-4-cyanophenol.

Preparation 3

3-(3,5-Difluoro-4-hydroxyphenyl)-5-trifluoromethyl-1,2,4-oxadiazole 0.1 mol 3,5-difluoro-4-methoxybenzonitrile, 0.3 ml of hydroxylamine hydrochloride and 0.3 mol of potassium carbonate were added to 400 mL ethanol and refluxed overnight. The product was filtered and recrystallized from methanol giving 3.04 g of 3,5-difluoro-4-methoxybenzamide oxime. This product was dissolved in 5 mL pyridine and 5.6 mL of trifluoroacetic anhydride was added dropwise at room temperature. Upon cooling the product solidified and was rinsed with water yielding 4.1 g of product (Formula III: $R_2=3\text{-fluoro}$, $R_3=5\text{-fluoro}$, $R_4=5\text{-trifluoromethyl-1,2,4-oxadiazol-3-yl}$.

Preparation 4

3-(4-Hydroxyphenyl)-5-trifluoromethyl-1,2,4-oxadiazole 13.32 g (0.1 mol) 4-methoxybenzonitrile, 20.85 g (0.3 mol) of hydroxylamine hydrochloride and 41.40 g (0.3 mol) potassium carbonate was added to 400 mL absolute ethanol and refluxed 21 hours. The product was filtered and recrystallized from methanol to give 3.12 g (0.02 mol) of 4-methoxybenzamide oxime.

This product was dissolved in 5 ml pyridine and 5.7 mL (0.04 mol) of trifluoroacetic anhydride was added dropwise at room temperature. Upon cooling, the mixture solidified and was rinsed with water yielding 4.3 g of product III wherein $R_2=R_3=\text{hydrogen}$; $R_4=5\text{-trifluoromethyl-oxadiazol-3-yl}$.

Preparation 5

Preparation of 4-piperidineethanol a) Ethyl 4-piperidylacetate was dissolved in 50 ml $CH_2Cl_2$ while chilling the mixture on an ice bath, 3.1 ml (22 mmol) triethylamine then benzyl chloride was added; the mixture was refluxed for 2 hours. After cooling the organic layer was extracted with water, brine and then dried over magnesium sulfate. After crystallization, 2.05 g of ethyl N-benzyl-4-piperidylacetate was obtained (Formula XI: $Y'=CH_2$, alkyl$=C_2H_5$).

b) 2 g (7.5 mmol) of this intermediate was taken up in THF and 0.4 g (10 mmol) $LiAlH_4$ in 5 ml methylene chloride was added. The mixture was stirred for 2 hours, then quenched with dropwise addition of water. The organic layer was dried over potassium carbonate, filtered and concentrated in vacuo to afford a yellow oil, which crystallized upon standing to afford N-benzyl-4-piperidineethanol (Formula V: Y=ethylene).

c) 4 mmol of this intermediate, 15 mmol (3 ml) of 5 M ammonium formate and a catalytic amount of palladium on carbon was suspended in 25 ml of methanol and refluxed for two hours. The products were then basified and extracted with methylene chloride the organic layer was washed with brine twice and then water, concentrated in vacuo and crystallized upon standing giving 4-piperidineethanol.

Preparation 6

Preparation of 4-piperidinemethanol a) Commercially available ethyl 4-isonipecotate was dissolved in 50 ml $CH_2Cl_2$ while chilling the mixture on an ice bath, 3.1 ml (22 mmol) triethylamine was added. After this addition benzyl chloride was added; the mixture was refluxed for 2 hours. After cooling the organic layer was extracted with water, brine and then dried over magnesium sulfate. After crystallization, 2.05 g of ethyl N-benzyl-4-isonipecotate was obtained (Formula XI: $Y'=\text{bond}$, alkyl$=\text{ethyl}$) 3 g (12 mmol) of this intermediate and 0.47 g (12 mmol) $LiAlH_4$ were reacted and worked up in a manner similar to that producing 4-piperidineethanol. The organic layer was dried over magnesium sulfate, filtered and concentrated in vacuo to afford a yellow oil, which crystallized upon standing, giving N-benzyl-4-piperidinemethanol (Formula V: Y=methylene).

b) 4 mmol of this intermediate, 15 mmol (3 ml) of 5 M ammonium formate and a catalytic amount of palladium on carbon was dissolved in 25 ml of methanol and refluxed for two hours. The products were then basified and extracted with methylene chloride the organic layer was washed with brine twice and then water, concentrated in vacuo and crystallized upon standing giving 4-piperidinemethanol.

Preparation 7

Preparation of 3-methyl-5-(4-(2-hydroxyethyl)-1-piperidyl)isoxazole a) A mixture of 9.81 g (100 mmol) of 5-amino-3-methylisoxazole, 200 mL NMP, 69 g potassium carbonate and 4.2 g potassium iodide and 64 mL (500 mmol) allyl acrylate was refluxed for 16 hours. Upon cooling the products were partitioned between ether and water. The water layer was washed twice with 250 mL ether and the organic layers were pooled. The organic layers were washed thrice with 1N HCl then brine and dried over magnesium sulfate and concentrated in vacuo, yielding 16.9 g of the bis ester

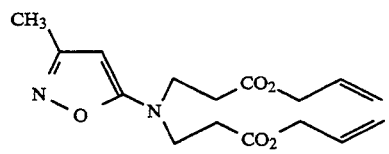

b) 16.1 g of this intermediate was taken up in dry benzene and added dropwise to sodium hydride, then refluxed for 30 minutes and cooled. 100 mL saturated ammonium chloride was added dropwise and then 14.2 mL water. The mixture was extracted thrice with ether, and the organics were combined, dried over magnesium sulfate and then concentrated in vacuo to give 8.59 g of the cyclized product

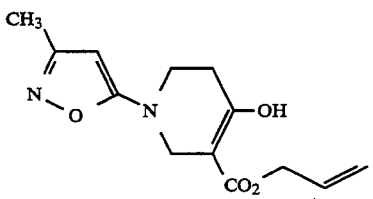

c) 7.93 g ( 3.0 mmol) of the above intermediate was taken up in THF, 2.62 mL (30 mmol) morpholine and 8.5 mg (76 mmol) tetrakis (triphenylphosphinyl) palladium was added and stirred for 5 minutes. 80 mL ether was added, upon drying a 68% yield (3.71 g) of the piperidinone

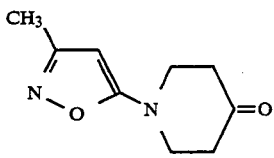

was obtained.

d) 3.75 g (20.8 mmol) of this intermediate was taken up in 20 mL THF and 4.86 mL (30 mmol) trimethylphosphonoacetate in 90 mL THF was added dropwise over 20 minutes. To this was added 20 mL 1.8 M LDA/THF in cyclohexane while the reaction mixture was kept at −78° C. The products were brought to room temperature and partitioned between 50 mL ether and 200 ml, water. The organic layer was washed with brine and then dried over magnesium sulfate and concentrated in vacuo, yielding 4.62 g of the ester

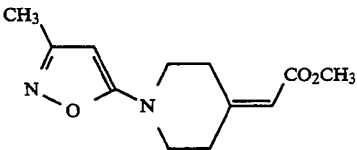

e) 7.2 g (40 mmol) copper(I) bromide in 75 mL THF was cooled to 0° C and 11.2 mL 70% NaAlH$_2$(OCH$_2$CH$_2$OCH$_3$)$_2$ in toluene was added dropwise. 8.0 mL of n-butanol and a solution of 0.18 g of the above intermediate in THF was stirred in for 30 minutes. The reaction was quenched with 25 mL water and the products poured into 100 mL saturated ammonium chloride. The aqueous layer was washed thrice with ether. The organic layer was pooled and washed with water, brine and then dried over magnesium sulfate, and concentrated in vacuo yielding

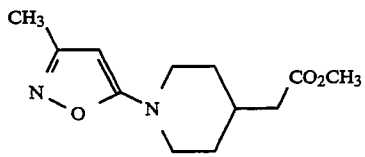

f) A solution of 0.33 g of the above intermediate was taken up in 4 mL THF and cooled to 0° C. 3.2 mL 1M diisobutylaluminum hydride in hexane was added dropwise over 15 minutes. The reaction was quenched with Rochelle's salt and 5 mL water. The organic layer was washed thrice with water and then brine, dried over magnesium sulfate and concentrated in vacuo, giving a quantitative yield of 3-methyl-5-(4-(2-hydroxyethyl)-1-piperidinyl)isoxazole (Formula II: R$_1$=3-methyl-5-isoxazolyl, Y=ethylene).

Preparation 8

20 mmol 5-methyl-2-bromopyridine and 15 mmol 4-piperidineethanol was taken up in 100 ml of a 1:1 mixture of NMP and diisopropyethylamine (DIPEA) and refluxed for 1 ½ hours; then cooled and allowed to stand overnight.

The products were extracted with 2N sodium hydroxide, then water thrice, dried over magnesium sulfate and concentrated in vacuo, yielding 1-(5-methyl-2-pyridyl)- 4-piperidineethanol (Formula II: R$_1$-5-methyl-2-pyridyl, Y=ethylene).

Preparation 9

Following a preparation similar to that described above in Preparation 8, but substituting the appropriate halopyridine, halopyrimidine or halopyrazine for 5-methyl-2-bromopyridine and substituting the appropriate piperidinol or piperidine alkanol for 4-piperidineethanol, the intermediates of formula II shown in Table 1 were prepared. In the table, pyr means pyridinyl, pym is pyrimidinyl and pyz is pryrazinyl. NMP/DIPEA refers to a 1:1 mixture of diisopropylethylamine and N-methyl pyrrolidine. Where n-butanol is listed as solvent, K$_2$CO$_3$ is added to the reaction mixture. Intermediates of formula II were used without further purification in the preparation of compounds of formula I.

TABLE 1

PREPARATION OF FORMULA II INTERMEDIATES

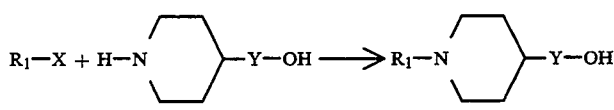

| Y = (CH$_2$)$_n$ n | mmol Piperidine/R$_1$—X | R$_1$ | X | Reflux Time | Reaction solvent | Yield (%) |
|---|---|---|---|---|---|---|
| 0 | 3/9 | 2-CH$_3$-4-pyr | Cl | 3.5 h | n-Butanol | 54 |
| 2 | 31/38 | 4-pyr | Cl | 24 h | n-Butanol | 61 |
| 2 | 23/28 | 2-CH$_3$-4-pyr | Cl | 24 h | DIPEA | 63 |
| 0 | 17/26 | 5-CH$_3$-2-pyr | Br | 4.5 h | NMP/DIPEA | 41 |
| 1 | 41/29 | 5-CH$_3$-2-pyr | Br | 2 h | NMP/DIPEA | 68 |
| 2 | 41/45 | 4-CH$_3$-2-pym | Cl | 6 h | NMP/DIPEA | 46 |
| 2 | 15/15 | 2-pyz | Cl | 24 h | NMP/DIPEA | 57 |

EXAMPLE 1

(Formula I: $R_1$=5-methyl-2-pyridyl, $R_2$=3-methyl, $R_3$=5-methyl, $R_4$=2-methyl-2H-tetrazol-5-yl, Y=$CH_2CH_2$)

9.8 moles of 2-methyl-5-(4-hydroxy-3,5-dimethylphenyl)-2H-tetrazole, 8.9 mmoles of 1-(5-methyl-2-pyridyl)-4-piperidineethanol and 2.57 g triphenyl phosphine (TPP) was taken up in 150 ml of methylene chloride and chilled on an ice bath. To this mixture a solution of 1.79 g diethyl azidocarboxylate (DEAD) in 2.5 mL methylene chloride was added dropwise over 30 min. After addition, the mixture was refluxed for 1 hour, then cooled. 50 mL water was added to quench the reaction and the aqueous layer was washed twice with methylene chloride and the organics were pooled and washed with 10% sodium hydroxide, brine and water, then dried over magnesium sulfate and concentrated in vacuo. The crude product was recrystallized from ethanol giving a 66% yield of a compound of Formula I ($R_1$=5-methyl-2-pyridyl, $R_4$=2-methyl-2H-tetrazol-5-yl, $R_2$=3-methyl, $R_3$=5-methyl, Y=$CH_2CH_2$), melting point 174°–176° C.

EXAMPLES 2-12

Following a procedure similar to that described in Example 1, but substituting for 2-methyl-5-(4-hydroxy-3,5-dimethylphenyl) -2H-tetrazole and 1-(5-methyl-2-pyridyl)- 4-piperidineethanol, the appropriate phenol of formula III and the appropriate piperidine of formula II, the compounds of formula I shown in Table 2 were prepared.

Abbreviations used in the table are as follows: Tet is (2H-tetrazolyl; Pyr is pyridyl, Pyz is pyrazinyl, Isox is isoxazolyl, DEAD is diethyl azidocarboxylate and TPP is triphenyl phosphine.

EXAMPLE 13

Preparation of the compound of formula I wherein $R_1$=5-methyl-2-pyridinyl, $R_2$=$R_3$=hydrogen, $R_4$=2-methyl-2H-tetrazol-5-yl, Y=ethylene )

a) 16.5 g (0.1 mol) Ethyl 4-pyridylacetate, 8.4 mL (0.1 mol) 12 N hydrochloric acid and 2.5 g platinum oxide were dissolved in absolute ethanol and hydrogenated at 40 psi hydrogen on a Parr shaker. After 1 hour, the contents of the vessel were filtered and concentrated in vacuo yielding 27.79 g of ethyl 4-piperidinylacetate.

b) This sample was dissolved in 100 mL methylene chloride with 13.8 mL (0.12 mol) of benzyl chloride under nitrogen. 16.7 mL (0.12 mol) of triethylamine was added dropwise while chilling the mixture over ice. At the end of the addition the mixture came to room temperature and was stirred overnight, the organic layer was extracted with water then base, then saturated salt. The organic layer was concentrated to an oil in vacuo. Crystals formed from the oil yielding (56%) 14.61 g of ethyl N-benzyl-4-piperidinylacetate (Formula XI: alkyl-=ethyl, Y'=methylene).

c) 14.40 g (0.055 mol) of this compound was taken up in 100 mL dry THF under nitrogen. 2.3 g (0.06 mol) lithium aluminum hydride was added slowly and the mixture stirred 18 hours at room temperature. The reaction was quenched with a water/diethyl ether mixture. The mixture was basified with sodium hydroxide, and the organic layer was dried over magnesium sulfate then concentrated to an oil in vacuo affording a quantitative yield of N-benzyl-4-(2-hydroxyethyl)-piperidine (Formula V: Y=ethylene).

d) 5.98 g (0.025 mol) of this alcohol was taken up in 125 mL methylene chloride at 0° C. 0.025 mol of each of the following was added: triphenylphosphine, 2-methyl-5-(4-hydroxyphenyl)-2-H-tetrazole, and dropwise diethylazidocarboxylate (in an additional 25 mL methylene chloride) under nitrogen. After this addition, the mixture was concentrated in vacuo and recrystallized from ethanol giving the intermediate

TABLE 2

PREPARATION OF COMPOUNDS OF FORMULA I

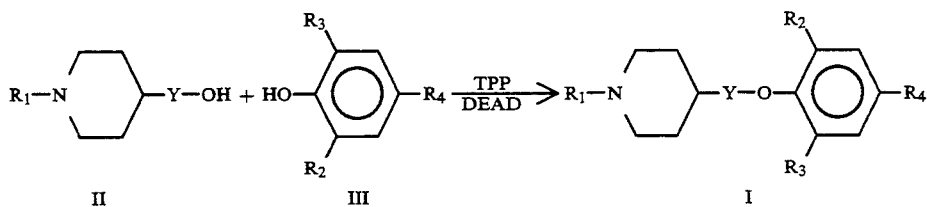

| Ex. # | $R_1$ | Y = $(CH_2)_n$<br>n = | $R_2/R_3$ | $R_4$ | mmoles<br>III/II | DEAD/<br>TPP (g) | Time | Recrystal<br>Solvent | Melting<br>point (C.) | Yield<br>(%) |
|---|---|---|---|---|---|---|---|---|---|---|
| 2 | 5-$CH_3$-2-Pyr | 0 | H/H | 2-$CH_3$-5-Tet | 8.6/7.8 | 1.5/2.26 | 2 h | ethanol | 122–123 | 64.9 |
| 3 | 5-$CH_3$-2-Pyr | 1 | H/H | 2-$CH_3$-5-Tet | 6.9/7.5 | 1.31/1.31 | 1 h | ethanol | 171–172 | 46 |
| 4 | 5-$CH_3$-2-Pyr | 1 | 3-$CH_3$/5-$CH_3$ | 2-$CH_3$-5-Tet | 7.0/6.4 | 1.22/1.22 | 18 h | ethanol | 160–161 | 78 |
| 5 | 4-Pyr | 2 | H/H | 2-$CH_3$-5-Tet | 8.9/9.7 | 3.0/3.05 | 72 h | Ethyl acetate | 125–127 | 30 |
| 6 | 2-$CH_3$-4-Pyr | 0 | 3-$CH_3$/5-$CH_3$ | 2-$CH_3$-5-Tet | 12/11 | 3.3/3.5 | 18 h | Isopropyl acetate | 143–145 | 26 |
| 7 | 2-$CH_3$-4-Pyr | 2 | 3-$CH_3$/5-$CH_3$ | 2-$CH_3$-5-Tet | 8.8/8.8 | 1.8/2.8 | 2 h | Isopropyl acetate | 190–191 | 69 |
| 8 | 4-Pyr | 2 | H/H | 1,3-oxazalin-2-en-2yl | 10.6/9.7 | 2.0/3.0 | 6 h | Isopropyl acetate | 108–109 | 7 |
| 9 | 5-$CH_3$-2-Pyr | 2 | H/H | $COOC_2H_5$ | 10.9/9.9 | 2.0/2.86 | ½ h | (none) | 99–101 | 76.4 |
| 10 | 2-$CH_3$-Isox | 2 | H/H | 2-$CH_3$-5-Tet | 2.51/1.4 | 0.5/0.69 | 24 h | (none) | 129–130 | 84 |
| 11 | 2-pyz | 2 | H/H | 2-$CH_3$-5-Tet | 2.48/2.48 | 0.43/0.659 | 10 min | (none) | 129 | 32 |
| 12 | 5-$CH_3$-2-Pyz | 2 | H/H | 2-$CH_3$-5-Tet | 0.687/0.669 | 0.121/0.183 | 24 h | Ethyl acetate | 125–126 | 50 |

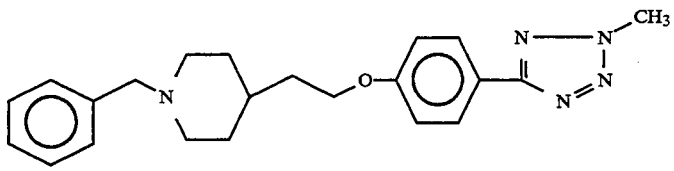

e) 3.91 g (9.64 mmol) of this intermediate, 7 mL (35 mmol) of 5M ammonium formate and a catalytic amount of palladium-on-carbon was dissolved in 50 mL of methanol and refluxed 1.5 hours. The mixture was concentrated and recrystallized from methanol yielding 1.63 g of the debenzylated product (Formula IV: $R_2=R_3=$hydrogen, Y=ethylene, $R_4=$2-methyl-2-H-tetrazol-5-yl).

f) 5.5 mmol of this product and 6.7 mmol 2-chloro-5-methylpyrimidine were taken up in 5 mL of 1:1 NMP/DIPEA and refluxed 6 hours, then cooled and allowed to stand overnight.

The reaction mixture was extracted 5 times with 25 mL ethyl acetate. The organic fractions were pooled and extracted with 2N sodium hydroxide then water thrice, dried over magnesium sulfate and concentrated in vacuo giving the product of formula I: $R_1=$5-methyl-2-pyrimidinyl, $R_2=R_3=$hydrogen, Y=ethylene, $R_4=$2-methyl-2-H-tetrazol-5-yl) in 46% yield.

EXAMPLE 14

Preparation of the compound of formula I:
$R_1=$4-chloro-5-methyl-2-pyrimidinyl,
$R_2=R_3=$hydrogen, $R_4=$2-methyl-2-H-tetrazol-5-yl,
Y=ethylene)

This compound was prepared as Example 13 using 700 mmol of 2,4-dichloro-5-methylpyrimidine and 700 mmol of the intermediate of Example 13e (Formula IV: Y=ethylene, $R_2=R_3=$hydrogen, $R_4=$2-methyl-2-H-tetrazol-5-yl) in 1:1 NMP/DIPEA and refluxing for 16 hours. Workup affords the product in 76% yield.

EXAMPLE 15

Preparation of the compound of formula I:
$R_1=$5-methyl-2-pyridyl, $R_2=R_3=$hydrogen,
$R_4=$2-methyl-2-H-tetrazol -5-yl, Y=ethylene 1.57 g (5.1 mmol) of the intermediate described in Example 13e (Formula IV: Y=ethylene, $R_2=R_3=$hydrogen, $R_4=$2-methyl-2-H-tetrazol-5-yl) and 4.3 g (25 mmol) 5-methyl-2-bromopyridine were taken up in 6 mL 1:1 NMP/DIPEA and heated at reflux for 2 hours. 50 mL water was added upon cooling. The product mixture was extracted thrice with ethyl acetate. The organic fractions were combined and washed thrice with water, then brine, then dried over magnesium sulfate and concentrated in vacuo. 4.9 g (57%) of a compound of Formula I was obtained ($R_1=$5-methyl-2-pyridyl, $R_2=R_3=$hydrogen, $R_4=$2-methyl-2-H-tetrazol-5-yl, Y=ethylene).

EXAMPLE 16

Preparation of the compound of formula I wherein
$R_1=$5-methyl-2-pyridyl, $R_2=R_3=$hydrogen,
$R_4=$5-methyl-1, 2,4-oxadiazol-3-yl, Y=ethylene A mixture containing equimolar amounts of 4-(2-hydroxyethyl)piperidine and 2-bromo-5-methylpyridine in a 1:1 mixture of diisopropylethylamine:N-methylpyrrolidine (NMP) is refluxed at 140° C for 4 hours. Upon cooling, 100 mL of water is added to the mixture and the contents are extracted with methylene chloride then washed twice with water and once with salt and evaporated in vacuo. The resulting oil is eluted through a short silica gel plug with 80% ethyl acetate and 20% hexanes and the solvents evaporated in vacuo, giving a compound of formula II ($R_1=$5-methyl-2-pyridyl, Y=ethylene).

This compound is taken up in a minimal amount of THF with equimolar amounts of triphenylphosphine (TPP) and 4-cyanophenol. An equimolar amount of diethyl azidocarboxylate (DEAD) dissolved in THF is added dropwise while cooling the stirred solution. At the end of the addition, the solution is allowed to come to room temperature and stirred overnight. The reaction mixture is diluted with methylene chloride and washed successively with water, 10% sodium hydroxide and saturated salt (NaCl). The organic layer is dried over magnesium sulfate and concentrated in vacuo. The resulting product may be recrystallized from methanol giving a compound of formula XII ($R_1=$5-methyl-2-pyridyl, $R_2=R_3=$hydrogen, Y=ethylene).

The above intermediate was combined with equimolar amounts of hydroxylamine hydrochloride, sodium acetate trihydrate, 25 mL ethanol and 5 mL water and heated to reflux for 2-8 hours. After concentrating the products in vacuo, 25 mL acetic anhydride is added to the residue and refluxed for 3 hours. The reaction is quenched by pouring the products into 400 mL of 10% sodium hydroxide in ice. the residue is extracted with methylene chloride, the solvent evaporated and the resulting product recrystallized in methanol to give the compound of Formula I wherein $R_1=$5-methyl-2-pyridyl, $R_2=R_3=$hydrogen, $R_4=$5-methyl-1, 2,4-oxadiazol-3-yl, Y=ethylene.

It is contemplated that the products of Preparations 3 and 4 can be reacted with any of the intermediates of formula II by the method of examples 1-12 to form compounds of formula I.

Biological Properties

Biological evaluation of compounds of Formula I shows that they possess antiviral activity. They are useful in inhibiting virus replication in vitro and are primarily active against picornaviruses, including enteroviruses, echovirus and coxsackie virus, and especially numerous strains of rhinoviruses. The in vitro testing of the compounds of the invent ion against picornaviruses showed that viral replication was inhibited at minimum inhibitory concentrations (MIC) ranging from about 0.01 to about 5 micrograms per milliliter.

The MIC values were determined by a standard plaque reduction assay as follows: HeLa (Ohio) cells in monolayers were infected at a concentration of virus to give approximately 80 plaques per monolayer in the virus control (no drug present). The compound to be tested was serially diluted and included in the agar-medium overlay and in some cases, during the adsorption period as well.

The MIC was determined to be that concentration of compound which reduced the number of plaques by 50% with respect to the untreated virus control.

In the standard test procedure, the compounds were tested against a panel of fifteen human rhinovirus (HRV) serotypes, namely HRV-2, -1A, , 1B, -6, -14, -21, -22, -15, -25, -30, -50, -67, -89, -86 and -41. The MIC value for each rhinovirus serotype was determined, and the efficacy of each compound was determined in terms of MIC50 and MIC80 values, which is the concentration of the compound required to inhibit 50% and 80%, respectively, of the tested serotypes.

Table 3 gives the test results of representative examples of the invention. The number of serotypes (N) is indicated in parentheses after the MIC80 figure.

TABLE 3

| Example | MIC$_{50}$ | MIC$_{80}$ | N = |
|---|---|---|---|
| 1 | 49.93 | 99 | 2 |
| 2 | 1.85 | 2.6 | 2 |
| 3 | 82.524 | 99 | 6 |
| 4 | 83.117 | 99 | 6 |
| 5 | 50.75 | 99 | 2 |
| 6 | 50.1 | 99 | 2 |
| 7 | 1.14 | 2.9 | 3 |
| 8 | 46.2029 | 99 | 7 |
| 9 | 0.52 | 0.63 | 2 |
| 10 | 42.503 | 99 | 14 |
| 11 | 23.262 | 50.87 | 13 |
| 12 | 77.585 | 99 | 13 |
| 13 | 66.144 | 99 | 12 |
| 14 | 41.553 | 99 | 12 |
| 15 | 0.205 | 0.26 | 2 |

The antiviral compositions are formulated for use by preparing a dilute solution or suspension in a pharmaceutically acceptable aqueous, organic or aqueous organic medium for topical or parenteral administration by intravenous or intramuscular injection, or for intranasal or ophthalmic application; or are prepared in tablet, capsule, or aqueous suspension form with conventional excipients for oral administration.

We claim:

1. A compound of the formula

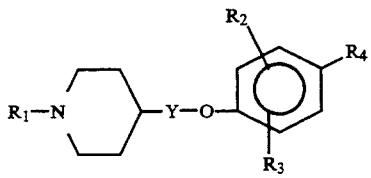

wherein
R$_1$ is selected from

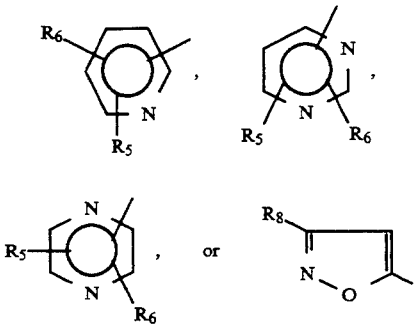

Y is a bond or lower-alkylene;
R$_2$ and R$_3$ are independently hydrogen, lower-alkyl or halogen;
R$_4$ is

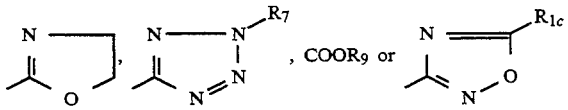

R$_5$ is hydrogen, lower-alkyl or halogen;
R$_6$ is hydrogen, lower-alkyl, or halogen;
R$_7$ is hydrogen or lower-alkyl;
R$_8$ is hydrogen, lower-alkyl, or trifluoromethyl;
R$_9$ is lower-alkyl; and
R$_{10}$ is lower-alkyl, trifluoromethyl or difluoromethyl;
or a pharmaceutically acceptable acid addition salt thereof.

2. A compound according to claim 1 where R$_1$ is

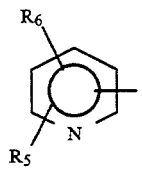

3. A compound according to claim 2 wherein Y is a bond, methylene or ethylene.

4. A compound according to claim 3 wherein R$_4$ is 2-R$_7$-5-tetrazolyl

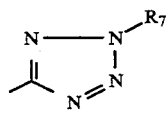

5. A compound according to claim 4 wherein R$_2$, R$_3$, R$_5$, and R$_6$ are hydrogen or lower-alkyl.

6. A compound according to claim 5 wherein R$_2$, R$_3$, R$_5$, R$_6$, and R$_7$ are hydrogen or methyl.

7. A compound according to claim 6 wherein R$_1$ is 5-methyl-2-pyridyl, R$_2$ and R$_3$ are hydrogen, R$_4$ is 2-methyl-5-tetrazolyl, and Y is a bond.

8. A compound according to claim 6 wherein R$_1$ is 2-methyl-4-pyridyl, R$_2$ is 5-methyl, R$_3$ is 3-methyl, R$_4$ is 2-methyl-5-tetrazolyl, and Y is ethylene.

9. A compound according to claim 6 wherein R$_1$ is 5-methyl-2-pyridyl, R$_2$ and R$_3$ are hydrogen, R$_4$ is 2-methyl-5-tetrazolyl and Y is ethylene.

10. A compound according to claim 3 wherein R$_4$ is COOR$_9$.

11. A compound according to claim 10 wherein R$_1$ is 5-methyl-2-pyridyl, R$_2$ and R$_3$ are hydrogen, R$_9$ is ethyl and Y is ethylene.

12. A composition comprising a pharmaceutical carrier and a compound according to claim 1 in an amount effective to combat picornaviral infection in a mammalian host.

13. A composition comprising a pharmaceutical carrier and a compound according to claim 5 in an amount effective to combat picornaviral infection in a mammalian host.

14. A composition comprising a pharmaceutical carrier and a compound according to claim 6 in an amount effective to combat picornaviral infection in a mammalian host.

15. A composition comprising a pharmaceutical carrier and a compound according to claim 7 in an amount effective to combat picornaviral infection in a mammalian host.

16. A composition comprising a pharmaceutical carrier and a compound according to claim 8 in an amount effective to combat picornaviral infection in a mammalian host.

17. A composition comprising a pharmaceutical carrier and a compound according to claim 9 in an amount effective to combat picornaviral infection in a mammalian host.

18. A composition comprising a pharmaceutical carrier and a compound according to claim 11 in an amount effective to combat picornaviral infection in a mammalian host.

19. A method of combating picornaviral infection which comprises administering to a mammalian host in need of such treatment an antipicornavirally effective amount of a compound according to claim 1.

20. A method of combating picornaviral infection which comprises administering to a mammalian host in need of such treatment in antipicornavirally effective amount of a compound according to claim 6.

21. A method of combating picornaviral infection which comprises administering to a mammalian host in need of such treatment an antipicornavirally effective amount of a compound according to claim 7.

22. A method of combating picornaviral infection which comprises administering to a mammalian host in need of such treatment an antipicornavirally effective amount of a compound according to claim 8.

23. A method of combating picornaviral infection which comprises administering to a mammalian host in need of such treatment an antipicornavirally effective amount of a compound according to claim 9.

24. A method of combating picornaviral infection which comprises administering to a mammalian host in need of such treatment an antipicornavirally effective amount of a compound according to claim 11.

* * * * *